(12) United States Patent
Cabiri

(10) Patent No.: US 11,027,070 B2
(45) Date of Patent: Jun. 8, 2021

(54) MEDICAL DEVICE FOR FLUID DELIVERY HAVING REDUCED DEAD SPACE

(71) Applicant: West Pharma. Services IL, Ltd., Ra'anana (IL)

(72) Inventor: Oz Cabiri, Hod Hasharon (IL)

(73) Assignee: WEST PHARMA SERVICES IL, LTD, Ra'anana (IL)

( * ) Notice: Subject to any disclaimer, the term of this patent is extended or adjusted under 35 U.S.C. 154(b) by 304 days.

(21) Appl. No.: 15/766,598

(22) PCT Filed: Oct. 10, 2016

(86) PCT No.: PCT/US2016/056218
§ 371 (c)(1),
(2) Date: Apr. 6, 2018

(87) PCT Pub. No.: WO2017/062932
PCT Pub. Date: Apr. 13, 2017

(65) Prior Publication Data
US 2018/0296763 A1    Oct. 18, 2018

Related U.S. Application Data

(63) Continuation of application No. 15/204,542, filed on Jul. 7, 2016, now Pat. No. 10,576,207, which is a (Continued)

(51) Int. Cl.
*A61M 5/28* (2006.01)
*A61M 5/142* (2006.01)
(Continued)

(52) U.S. Cl.
CPC ............ *A61M 5/28* (2013.01); *A61M 5/3134* (2013.01); *A61M 5/3202* (2013.01);
(Continued)

(58) Field of Classification Search
CPC .... A61M 5/28; A61M 5/3134; A61M 5/3202; A61M 5/3204; A61M 5/14248; A61M 5/1456
See application file for complete search history.

(56) References Cited

U.S. PATENT DOCUMENTS 1,125,887 A    1/1915   Schimmel
1,321,550 A    11/1919  Platt
(Continued)

FOREIGN PATENT DOCUMENTS

DE    855313 C     11/1952
EP    2364739 A1   9/2011
(Continued)

OTHER PUBLICATIONS

Int'l Search Report and Written Opinion dated Dec. 2, 2016 in Int'l Application No. PCT/US2016/056210.
(Continued)

*Primary Examiner* — Nathan R Price
*Assistant Examiner* — Tasnim Mehjabin Ahmed
(74) *Attorney, Agent, or Firm* — Panitch Schwarze Belisario & Nadel LLP

(57) ABSTRACT

Disclosed herein is a pharmaceutical syringe having a cylindrical bore with a proximal opening, the syringe comprising a distal wall of the bore defining an outlet biased from the central axis of the syringe, and toward a first area of the distal wall and biased from the central axis away from a second area distinct from the first area; the syringe comprising a plunger seal having a distal surface; wherein when the plunger seal is fitted into the bore with the distal surface facing an inner surface of the distal wall of the bore, the second area of the inner surface is axially closer to the distal surface of the plunger seal than the first area, in a direction
(Continued)

parallel to the central axis of the cylindrical bore, such that fluid is expelled from the second area and towards the outlet.

20 Claims, 10 Drawing Sheets

Related U.S. Application Data continuation of application No. 15/269,248, filed on Sep. 19, 2016, now Pat. No. 10,086,145, which is a continuation-in-part of application No. 14/861,478, filed on Sep. 22, 2015, now Pat. No. 9,987,432.

(60) Provisional application No. 62/281,536, filed on Jan. 21, 2016, provisional application No. 62/284,806, filed on Oct. 9, 2015.

(51) Int. Cl.
| | |
|---|---|
| *A61M 5/145* | (2006.01) |
| *A61M 5/32* | (2006.01) |
| *A61M 5/31* | (2006.01) |
| *A61M 5/34* | (2006.01) |
| *B65D 1/36* | (2006.01) |
| *B65D 25/10* | (2006.01) |
| *B65D 5/50* | (2006.01) |
| *B65D 21/02* | (2006.01) |
| *A61M 5/158* | (2006.01) |

(52) U.S. Cl.
CPC .......... *A61M 5/3204* (2013.01); *A61M 5/34* (2013.01); *B65D 1/36* (2013.01); *B65D 5/503* (2013.01); *B65D 21/0233* (2013.01); *B65D 25/108* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2205/3306* (2013.01); *A61M 2207/00* (2013.01)

(56) References Cited

U.S. PATENT DOCUMENTS

| | | | |
|---|---|---|---|
| 4,704,105 A * | 11/1987 | Adorjan | A61M 5/315 604/222 |
| 4,710,178 A | 12/1987 | Henri et al. | |
| 5,275,582 A * | 1/1994 | Wimmer | A61M 5/31513 604/218 |
| 5,858,001 A | 1/1999 | Tsals et al. | |
| 6,186,979 B1 | 2/2001 | Dysarz | |
| 6,189,292 B1 | 2/2001 | Odell et al. | |
| 6,500,150 B1 | 12/2002 | Gross et al. | |
| 6,719,141 B2 | 4/2004 | Heinz et al. | |
| 6,824,529 B2 | 11/2004 | Gross et al. | |
| 6,843,782 B2 | 1/2005 | Gross et al. | |
| 7,967,795 B1 | 6/2011 | Cabiri | |
| 8,603,028 B2 | 12/2013 | Mudd et al. | |
| 8,721,603 B2 | 5/2014 | Lundquist | |
| 2001/0025168 A1* | 9/2001 | Gross | A61M 5/14248 604/506 |
| 2004/0122369 A1* | 6/2004 | Schriver | A61M 5/14546 604/152 |
| 2005/0154353 A1 | 7/2005 | Alheidt | |
| 2009/0093792 A1 | 4/2009 | Gross et al. | |
| 2013/0131589 A1 | 5/2013 | Mudd et al. | |
| 2013/0253434 A1 | 9/2013 | Cabiri | |
| 2014/0163526 A1 | 6/2014 | Cabiri et al. | |
| 2015/0112278 A1 | 4/2015 | Ray et al. | |
| 2015/0157806 A1 | 6/2015 | Knutsson | |

FOREIGN PATENT DOCUMENTS

| | | |
|---|---|---|
| EP | 2452708 A1 | 5/2012 |
| JP | 2002505601 A | 2/2002 |
| JP | 2011136153 A | 7/2011 |
| JP | 2015514486 A | 5/2015 |
| WO | 9721457 A1 | 6/1997 |
| WO | 9857683 A1 | 12/1998 |
| WO | 2005070485 A1 | 8/2005 |
| WO | 2009043000 A1 | 4/2009 |
| WO | 2011110872 A1 | 9/2011 |
| WO | 2013036602 A1 | 3/2013 |
| WO | 2016087626 A1 | 6/2016 |
| WO | 2016087627 A1 | 6/2016 |

OTHER PUBLICATIONS

Written Opinion dated Sep. 11, 2017 in Int'l Application No. PCT/US2016/056218.

Int'l Preliminary Report on Patentability date Jan. 8, 2018 in Int'l Application No. PCT/US2016/056218.

Office Action dated Jul. 28, 2020 in Japanese Application No. 2018-538074.

* cited by examiner

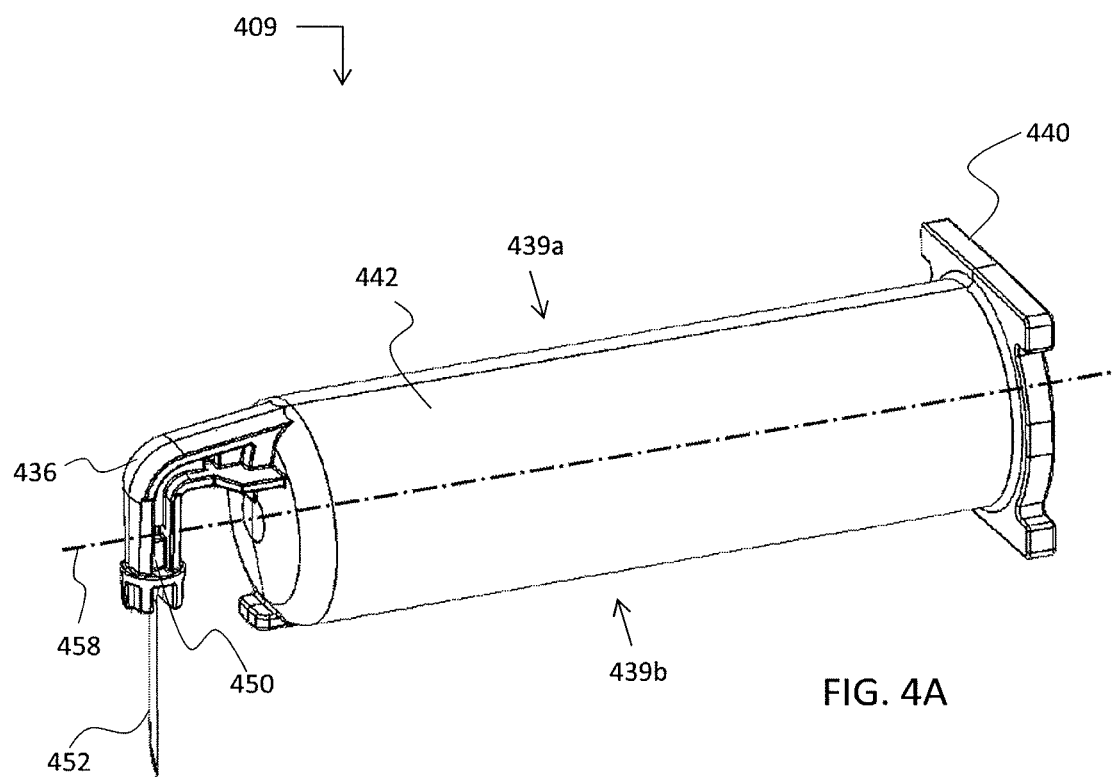

MEDICAL DEVICE FOR FLUID DELIVERY HAVING REDUCED DEAD SPACE

This application is a section 371 of International Application No. PCT/US16/56218, filed Oct. 10, 2016, which was published Apr. 13, 2017 Under International Publication No. WO 2017/062932 A1, which is a continuation of U.S. application Ser. No. 15/204,542, filed Jul. 7, 2016, which claims the benefit of U.S. Provisional Application No. 62/281,536, filed Jan. 21, 2016 and U.S. Provisional Application No. 62/284,806, filed Oct. 9, 2015; and a continuation of U.S. application Ser. No. 15/269,248, filed Sep. 19, 2016, the disclosures of which are incorporated herein by reference.

FIELD AND BACKGROUND OF THE INVENTION

The present invention, in some embodiments thereof, relates to an angled syringe and, more particularly, but not exclusively, to an angled syringe having reduced fluid dead space.

U.S. Pat. No. 6,500,150 discloses, "A drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 6,824,529 discloses "a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 6,843,782 discloses, "A drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 5,858,001 discloses "A liquid drug delivery device" . . . "adapted to be adhered to the skin of a subject by a base member defining a skin-contacting surface having an adhesive coating. A columnar cartridge serves as reservoir for the drug and is incorporated in a housing which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject."

U.S. Patent Publication No. 20140163526 discloses that, "an automated injection device may be loaded with a standard type syringe and/or hypodermic needle. Optionally the syringe may be supplied loaded with medicine and/or covered with a sterile needle cover. The syringe may be loaded into the injector with in a sterile state with needle cover in place. Injector may include for example a fastener (for example an adhesive base). In some embodiments, the fastener may assist a user to hold injector steady on the skin of a patient for an extended period. For example, injector may be used to give injections of volume ranging between 0.5 and 3.0 ml over a time period ranging between 30 sec to 180 sec."

Additional background art includes U.S. Pat. No. 6,189,292. U.S. Patent Publication No. 20130253434, U.S. Patent Publication No. 2009/093,792, U.S. Pat. No. 7,967,795.

SUMMARY OF THE INVENTION

Example 1

A pharmaceutical syringe having a cylindrical bore with a proximal opening, the cylindrical bore having a central axis, the syringe comprising: a distal wall of the bore defining an outlet, the outlet biased from the central axis toward a first area of the distal wall and biased from the central axis away from a second area distinct from the first area; and a plunger seal having a perimeter sized and shaped to fit the cylindrical bore with the plunger seal coaxial to the cylindrical bore, the plunger seal having a distal surface; wherein when the plunger seal is fitted into the bore with the distal surface facing an inner surface of the distal wall of the bore, the second area of the inner surface is axially closer to the distal surface of the plunger seal than the first area, in a direction parallel to the central axis of the cylindrical bore.

Example 2

The pharmaceutical syringe of example 1, wherein a mean direction of the inner surface is tilted with respect to the central axis.

Example 3

The pharmaceutical syringe of example 2, wherein the mean direction of the inner surface is tilted at an angle ranging from about 1 to about 5 degrees with respect to the central axis.

Example 4

The pharmaceutical syringe of any of examples 1-3, wherein the second area of the inner surface is axially closer to the distal surface of the plunger seal allowing contacting at least 40% of the distal surface of the plunger before the distal surface contacts the first area.

Example 5

The pharmaceutical syringe of any of examples 1-4, wherein the distal face of the plunger seal comprises a convex shape.

Example 6

The pharmaceutical syringe of example 5, wherein the inner wall comprises a concave shape.

Example 7

The pharmaceutical syringe of example 6, wherein the inner wall comprises a conical shape, and wherein an opening angle of the inner wall is less sharp than an opening angle of the convex shape of the distal face of the plunger seal.

Example 8

The pharmaceutical syringe of any of examples 1-7, wherein the inner surface is not radially symmetrical.

Example 9

The pharmaceutical syringe of any of examples 1-8, wherein a mean direction of the first area of the inner surface is angled away from a mean direction of the distal surface of the plunger seal, when the plunger seal being coaxial to the bore.

Example 10

The pharmaceutical syringe of any of examples 1-8, wherein a mean direction of the second area of the inner wall is angled towards a mean direction of the distal surface of the plunger seal, when the plunger seal being coaxial to the bore.

Example 11

The pharmaceutical syringe of any of examples 1-10, wherein the axially closer comprises a distance between a mean outer edge of the distal surface of the plunger and a mean outer edge of the second area being smaller than a distance between the mean outer edge of the distal surface of the plunger and a mean outer edge of the first area.

Example 12

The pharmaceutical syringe of any of examples 1-11, wherein a transition between a surface of the first area of the inner surface and a surface of the second area of the inner surface is continuous.

Example 13

The pharmaceutical syringe of any of examples 1-12, wherein the first area of the inner wall comprising the biased fluid outlet is located in proximity to an edge of the bore and the second area is located in proximity to the opposite edge of the bore.

Example 14

The pharmaceutical syringe of any of examples 1-13, further comprising a bent fluid path originating from the biased fluid outlet.

Example 15

A method for reducing fluid dead space in a pharmaceutical syringe having a cylindrical bore with a proximal opening and a distal biased fluid outlet, the cylindrical bore fitting a plunger seal, the method comprising: driving the plunger seal towards the distal end of the cylindrical bore; contacting a portion of a distal surface of the plunger seal with a portion of an inner surface of a wall of the distal end of the bore at a contact area distinct from an area comprising the biased fluid outlet; and expanding a range of contact from the contact location towards the location of the biased fluid outlet while expelling fluid in a mean direction which is tilted with respect to a mean direction of the distal surface of the plunger.

Example 16

The method of example 15, wherein the contacting comprises initially contacting at the contact area being a peripheral edge of the inner surface, the peripheral edge being distinct to the area comprising the biased fluid outlet.

Example 17

The method of example 15, wherein the contacting at the contact area comprises contacting at least 40% of the distal surface of the plunger before contacting the area comprising the biased fluid outlet.

Example 18

The method of any of examples 15-17, wherein the expanding comprises expanding the range of contact from the peripheral edge, through a center portion of the inner wall and onto the area comprising the biased fluid outlet.

Example 19

The method of any of examples 15-18, wherein the expanding the range of contact is conducted by elastically deforming the plunger seal.

Example 20

The method of any of examples 15-19, wherein the expanding the range of contact results in driving fluid away from the contact location towards the location of the biased fluid outlet.

Example 21

The method of any of examples 15-20, further comprising ending the driving of the plunger seal at a force ranging between about 5 N and about 25 N.

Example 22

The method of example 21, wherein following the ending, a volume of a fluid dead space between the plunger seal and the inner wall ranges between about 0.01 ml and about 0.5 ml.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4B are schematic illustrations of a syringe having an off-centered fluid outlet, as being used in some embodiments of the current invention, wherein FIG. 4A is a perspective view and FIG. 4B is a cross-section taken across the dorsal-ventral longitudinal axis of the syringe;

Figures 5, 5A:
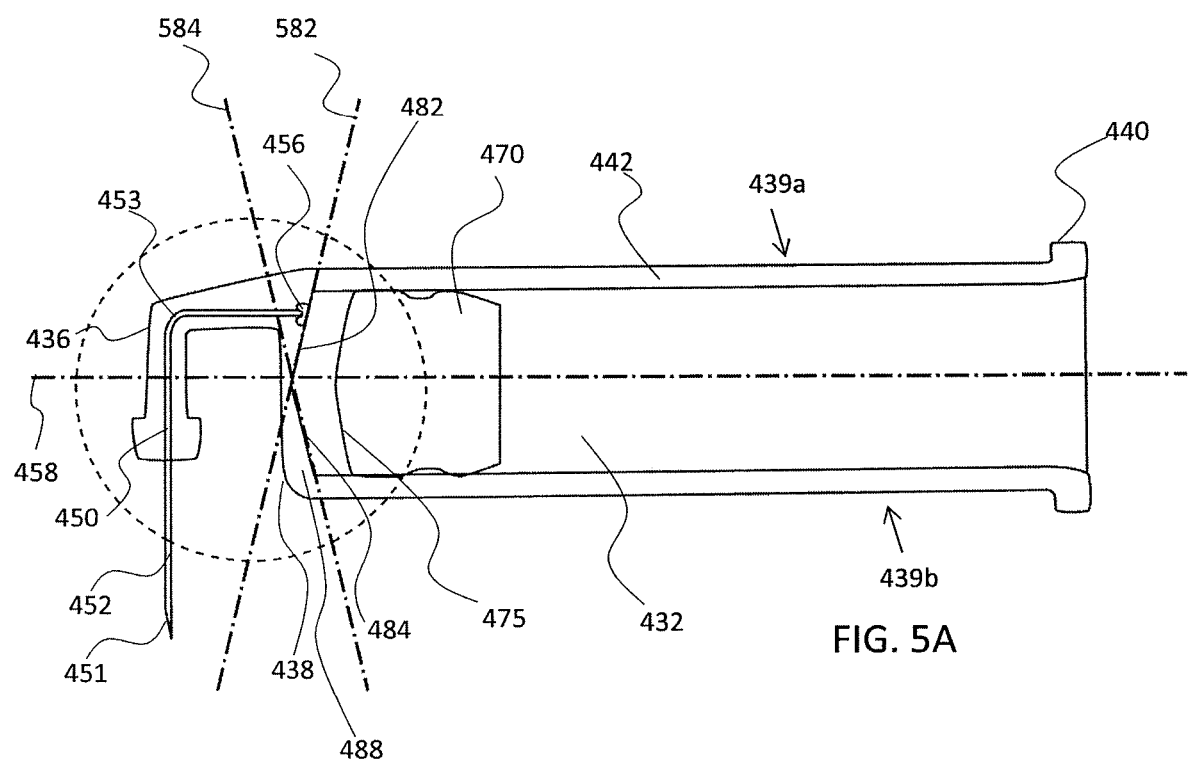
Figure 5B:
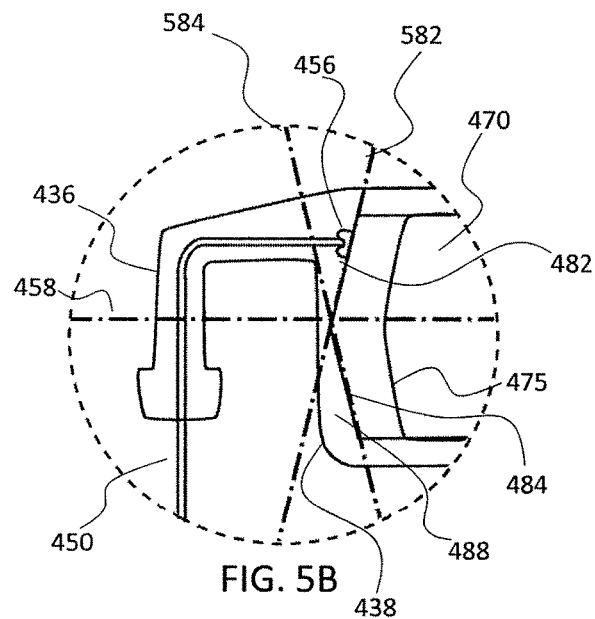
Figure 5C:
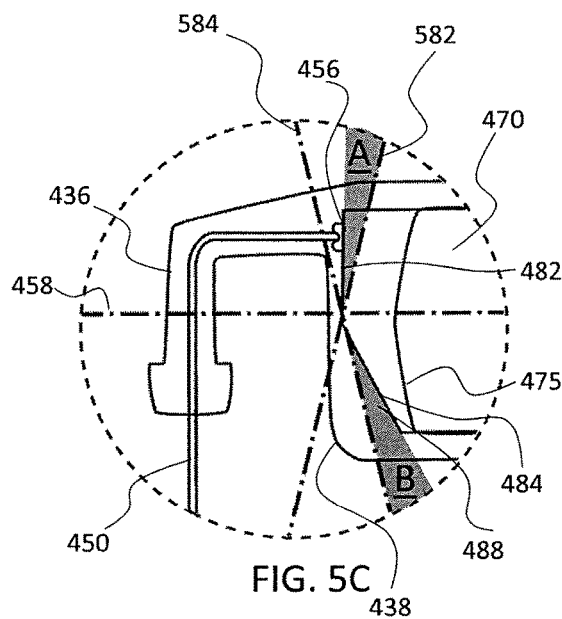
Figure 5D:
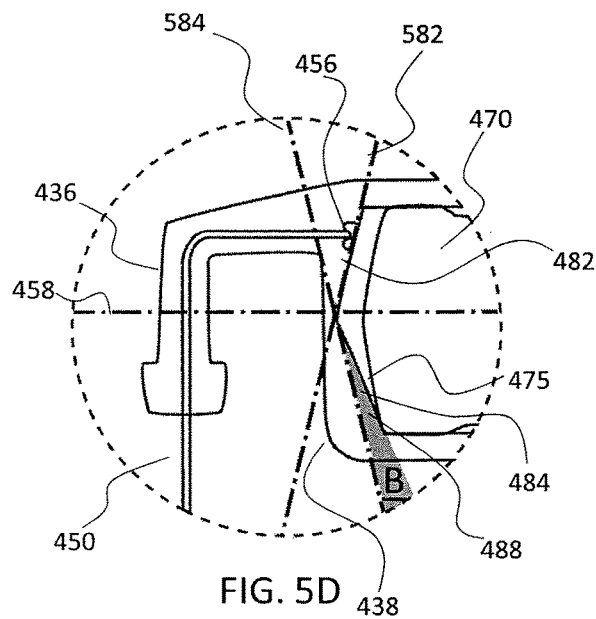
Figure 5E:
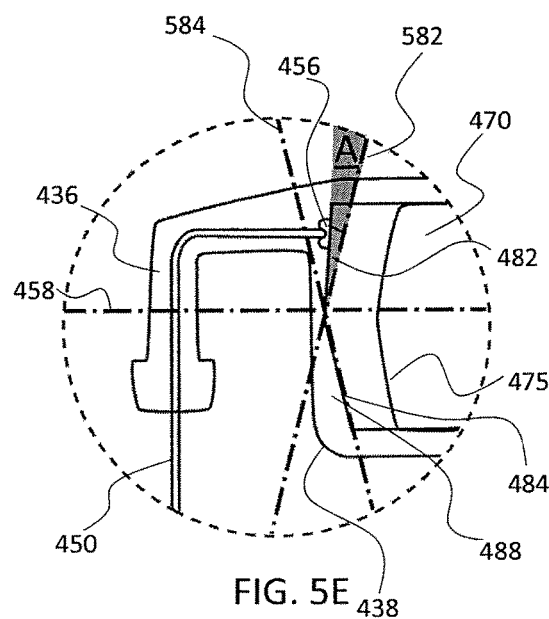
Figure 6:
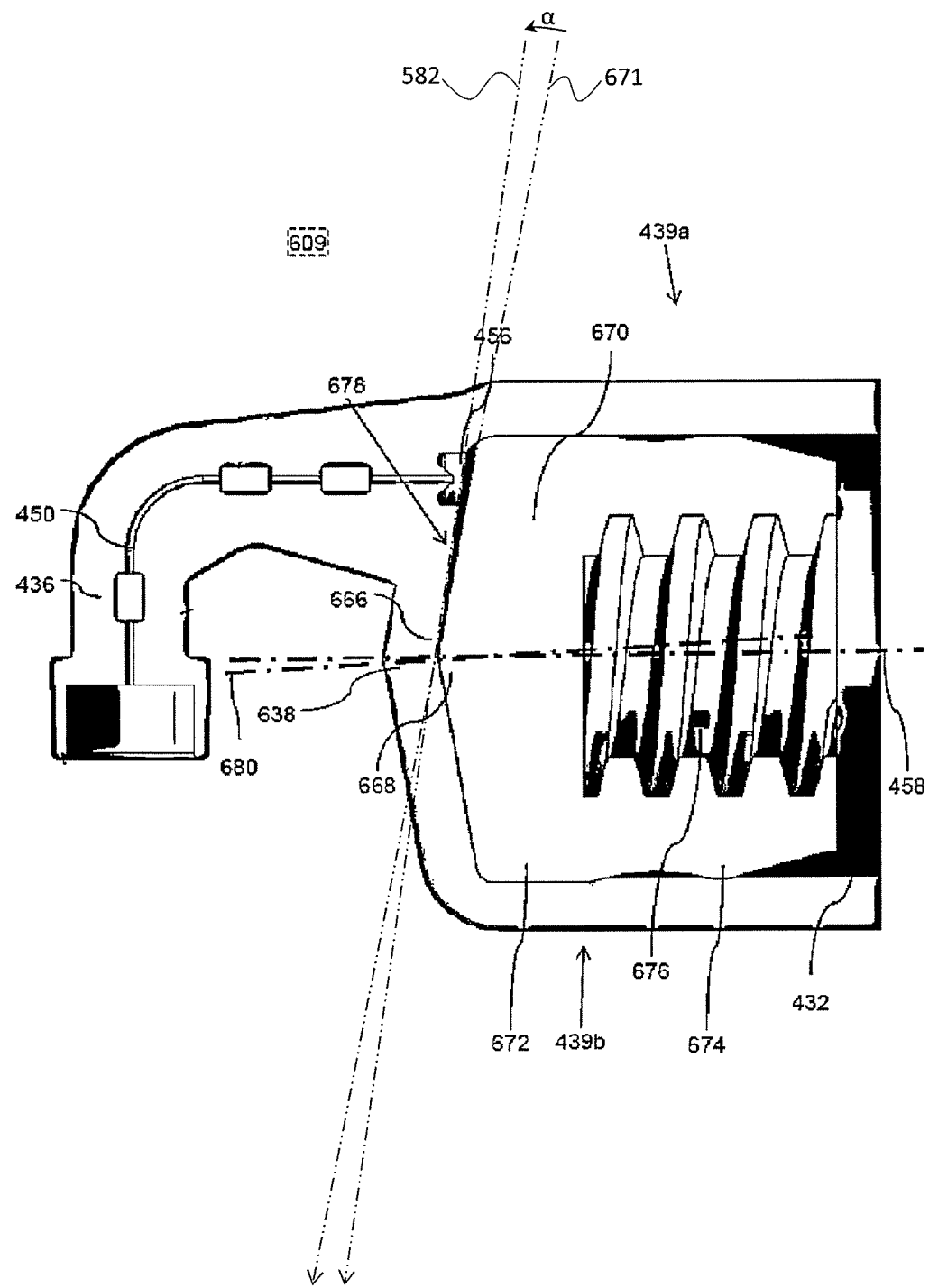
Figure 7:
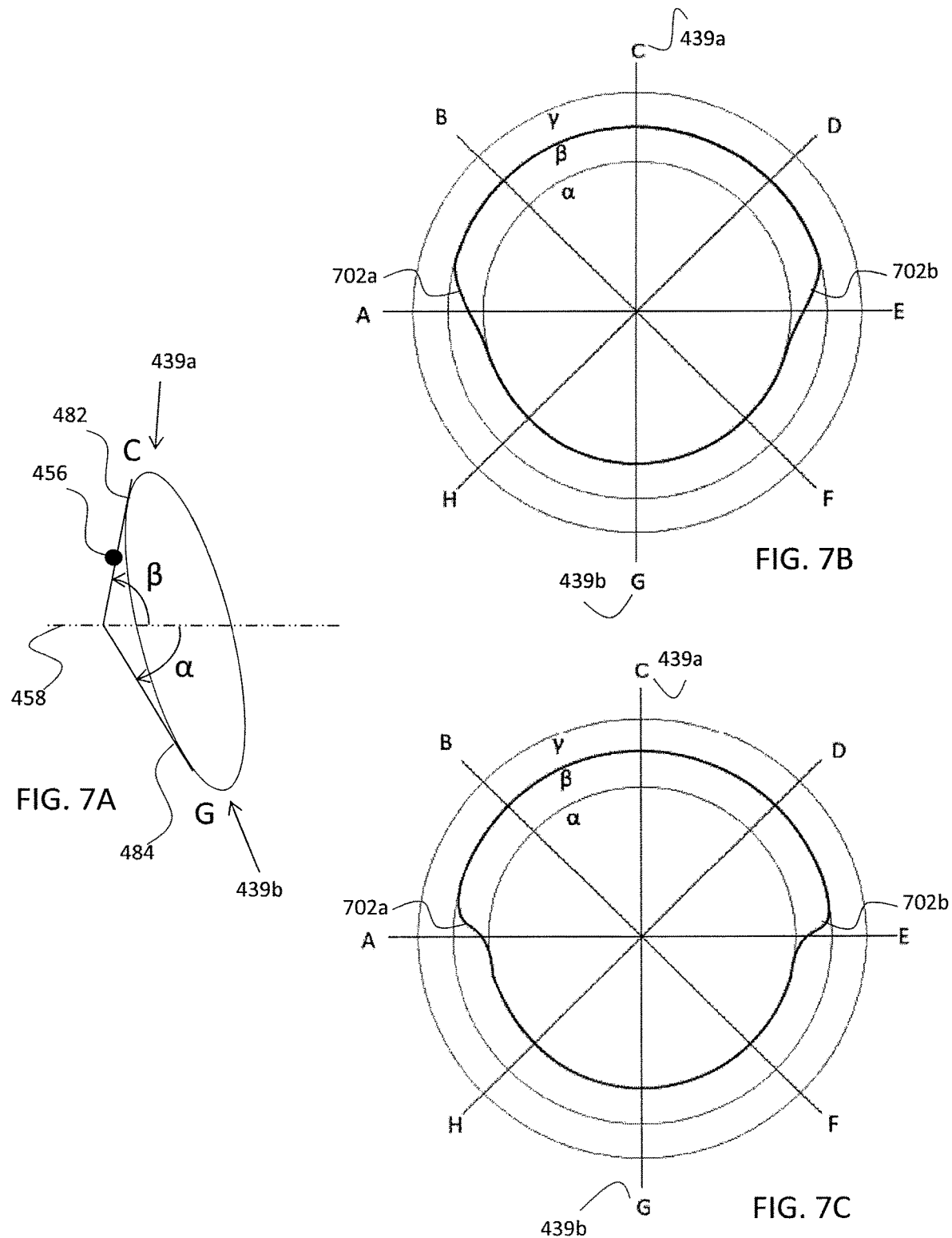
Figure 8:
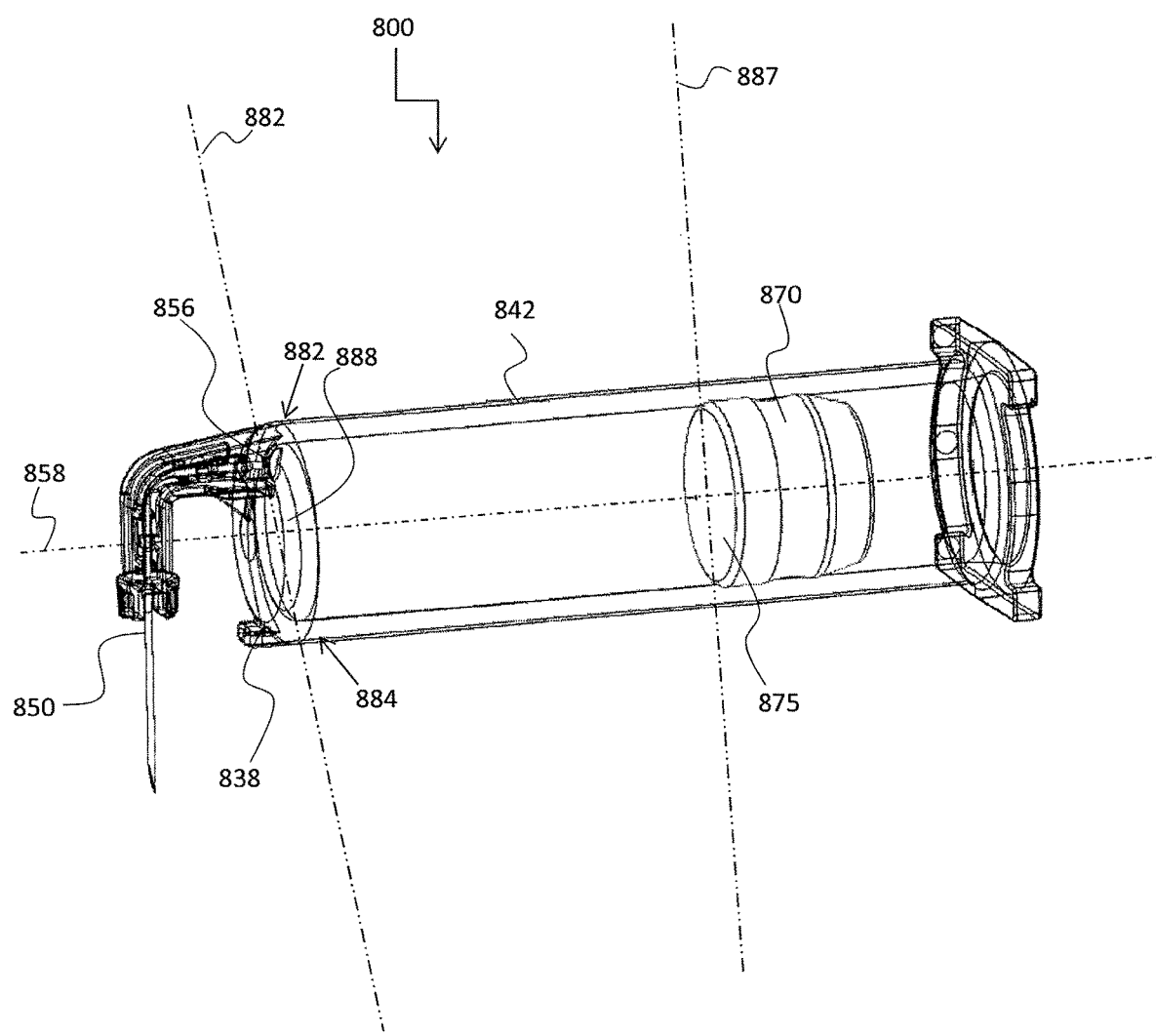

FIGS. 5A-5E are schematic illustrations showing a cross-section of a syringe having an off-centered fluid outlet at its distal end and various orientations of a concave inner wall of the distal end with respect to the longitudinal axis of the syringe, in accordance with some embodiments of the invention, wherein FIG. 5A illustrates an overview of a syringe with a non-modified inner wall, FIG. 5B illustrates a magnified portion of the marked area in FIG. 5A, FIG. 5C illustrates a tilted concave inner wall, FIG. 5D illustrates a concave inner wall having a tilted ventral portion and FIG. 5E illustrates a concave inner wall having a tilted dorsal portion;

FIG. 6 is a schematic illustration of a cross section of a tilted inner wall being contacted by a plunger seal, in accordance with some embodiments of the invention;

FIGS. 7A-7C are illustrations of the tilting angles comprised in the tilted inner wall, in accordance with some embodiments of the invention, wherein FIG. 7A schematically illustrates a cross-section of a tilted inner wall together with the longitudinal axis of the syringe, FIG. 7B illustrates a polar chart exemplifying continuous transition between different tilting angles and FIG. 7C illustrates a polar chart exemplifying a step transition between different tilting angles; and FIG. 8 is a schematic illustration showing a perspective view of an embodiment including a deformable flat faced plunger and a tilted inner wall of the syringe, in accordance with some embodiments of the invention.

DESCRIPTION OF SPECIFIC EMBODIMENTS OF THE INVENTION

The present invention, in some embodiments thereof, relates to an angled syringe and, more particularly, but not exclusively, to an angled syringe having reduced fluid dead space.

Overview

An aspect of the present invention relates to an asymmetric syringe having a reservoir for containing fluid and having a reduced fluid dead space. In some embodiments, a plunger seal is fitted into a syringe bore to drive fluid from the proximal portion of the bore and towards an off-center outlet fluid path provided in the distal portion of the bore. Potentially reducing fluid dead space, in some embodiments, the distal inner wall of the reservoir is shaped to drive fluid towards an off-center outlet fluid path, when being contacted by the plunger seal. For example, the plunger seal may be configured to contact a peripheral portion of the distal inner wall of the reservoir before contacting a central portion of the wall, followed by contacting the opposite peripheral portion of the wall which contains the fluid path exiting the bore. Optionally an expanding plunger-wall contact expels the fluid toward the uncontacted portions, thereby eliminating the fluid towards the off center outlet fluid path.

As used herein, the term dead space refers to the volume of fluid remaining within the medicinal syringe once the plunger can no longer be driven any further towards the distal end of the syringe. Typically, fluid remains within the needle and/or between the syringe hub and the plunger. Potential disadvantages of a relatively high fluid dead space include a waste of medication, and/or inaccurate dosing and/or potential disease transmission.

In some embodiments, the distal wall and/or the inner distal wall of the reservoir is angled slightly towards the edge containing the needle. Optionally this may improve drainage into an eccentrically located needle. Alternatively or additionally, the inner distal wall is angled slightly towards the plunger to create an initial contact location which is offset to the location of the fluid outlet, potentially resulting in fluid being driven from the offset location towards the outlet.

In some embodiments, a cartridge including a fluid reservoir may be designed to reduce dead space. For example, a plunger may be user to drive fluid out from the reservoir. For example, the plunger may drive fluid towards a distal wall of the reservoir. Optionally fluid may pass through an opening in the distal wall to the fluid path of an extension leading to the syringe needle. Optionally the plunger may be designed to initially contact a first portion of the distal wall being farthest from the opening, and gradually increase contact with the distal wall while being driven towards the wall. For example, as the plunger moves distally after first contacting the wall, an increasing surface of the wall may contact the plunger. For example as the contact surface increases, fluid may be driven along the distal wall towards the opening.

In some embodiments, the plunger is being driven by a motor, optionally having a rotational advancing mechanism. A standard plunger would probably be designed to expel fluid from a centrically located outlet. Therefore, in standard syringes with a centrically located outlet, the plunger's distal surface, defined by the surface being most proximal to the outlet, is likely to be radially symmetrical around the central axis of the bore, optionally having a standard convex shape. In some embodiments, the syringe as provided in the current application is configured to allow non-concentric fluid expulsion using a standard plunger having a radial symmetry.

For example, the distal inner wall of the reservoir may be conical and/or concave while the plunger seal may be conical and/or convex with a sharper opening angle than the opening angle of the distal inner wall of the syringe.

Alternatively, the distal surface of the plunger is substantially flat. Optionally the inner distal wall of the syringe may be angled with respect to the plunger seal and/or the axis of the bore. For example, the distal inner wall of the bore may be angled to contact the plunger seal on a side opposite the outlet fluid path before contacting the plunger seal on the side of the fluid outlet, for example by having the opposite side being axially closer to the plunger distal face along the longitudinal axis of the syringe bore. In some embodiments, the inner distal wall is angled by having its longitudinal axis being angled with respect to a longitudinal axis of the distal face of the plunger. For example, the longitudinal axis of the inner wall may be angled at an angle ranging from about 0.5° to about 2°, and/or about 2° to about 5°, and/or about 5° to about 10°, and/or any range smaller, larger or intermediate.

For example, at the end of travel of the plunger towards the distal wall of the cylinder under a force of ranging between about 0-5 N and/or between about 10-15 N and/or between about 15-25 N, the dead space between the plunger and the distal wall of the cylinder may range between about 0.01 to 0.05 and/or about 0.05 to 0.1 and/or between about 0.1 to 0.5 ml. Optionally, the volume of the fluid path between the reservoir and the exit opening of the fluid path in a distal section of the extension may be small. For example, the internal volume of the fluid path from the reservoir to the opening of the extension may range between 0 to 0.01 and/or 0.01 to 0.03 and/or 0.03 to 0.06 and/or 0.06 to 0.1 and/or 0.1 to 0.5 ml.

In some embodiments, the inner distal wall of the syringe bore is symmetrical, optionally around the central axis of the cylindrical bore. Alternatively or additionally the inner distal wall of the syringe bore is not symmetrical. Optionally, only a portion of the inner distal wall is angled. For example, in some embodiments the peripheral side comprising the fluid outlet is angled away from the distal face of the plunger, optionally while the opposite peripheral side fits the profile of the plunger face. Alternatively, the opposite peripheral side is angled towards the plunger face, optionally while the peripheral side comprising the fluid outlet fits the profile of the plunger face.

In some embodiments, angling of a portion and/or area and/or side of the inner wall is defined by the mean direction of the area, and its inclination and/or tilting relative to the central axis of the bore. In typical syringes having a concentric outlet, the mean direction of the inner distal wall of the bore is perpendicular to the central axis of the bore. In some embodiments, the inner distal wall is tilted such that the mean direction of the entire inner distal wall defines an angle which is greater than 90° relative to the central axis. Optionally, at least one area of the inner wall is shaped to substantially fit the plunger distal surface while at least a distinct area of the inner wall is angled away or towards the distal surface of the plunger. In some embodiments, the tilting of the at least one area of the inner wall with respect to the plunger, results in an area of the inner wall being closer to the plunger distal surface. As used herein, how close the inner wall and the plunger are, is defined by the distance between the mean outer edge of the distal inner wall (or a portion thereof) and the mean outer edge of the distal surface of the plunger. In some embodiments, a contact area being closer to the distal surface of the plunger is provided as closer than the fluid outlet area by a distance of 0.05-0.1 mm, 0.1-0.3 mm, or 0.2-0.4 mm or any range larger, smaller or intermediate.

In some embodiments, a first area comprises the fluid outlet and a second area, distinct from the first area, is shaped to contact the plunger first. In some embodiments, the second area of the inner surface is axially closer to the distal surface of the plunger seal, such that it allows contacting at least 40% of the distal surface of the plunger, before the distal surface contacts the first area. Alternatively, the proximity of the second area allows at least 30%, or at least 20%, or at least 50% of contact with the distal face of the plunger seal.

In some embodiments, the second area of the inner surface comprises 80% of the inner surface, not having the fluid outlet. Alternatively, the second area comprises at least 90%, and/or at least 95%, and/or at least 99% of the inner surface. In some embodiments, the first area comprises a connected area containing the fluid outlet. Optionally, the first area is less than 2% of the distal surface, and/or less than 5%, and/or less than 10%.

Alternatively or additionally, the distal surface of the plunger expels fluid from the second area, before sealing to the inner surface in a way that separates the first area from the second area. In some embodiments, other asymmetric configurations of the inner wall are provided. For example, the inner wall, in some embodiments, has the shape of a non-right cone, and/or has portions which are made of a combination of conical structures. For example, a first side of the inner wall is optionally shaped as a portion of a first cone having a first apex angle, and the second side of the inner wall is optionally shaped as a portion of a second cone having a second apex angle. Optionally, the first and second apex angles are not the same. Optionally, the diameter defined by the bases of the first cone and the second cone are not the same. In some embodiments, a sharper apex angle is provided at the side opposite to the fluid outlet, potentially angling this side to meet the plunger face before the side having the less sharp apex angle. In some embodiments, the transition between the first cone wall and the second cone wall is continuous. Alternatively or additionally, the transition is substantially a step transition.

The plunger seal optionally has a round cross section. For example, the plunger seal may be made of Chlorobutyl coated with PTFE layer, and/or Bromobutyl or EPDM or other suitable sealing material and/or material suitable for use with a drug product and the syringe over the product shelf life. In some embodiments, the plunger is made of a substantially deformable material, configured to deform when being pressed over the distal inner wall of the bore and match its surface.

In some embodiments, asymmetrical contact surface with the plunger distal surface is provided by molding and/or adding a layer to an area of the inner distal wall being offset to the fluid outlet. Optionally, a layer is added to create a contact area which is axially closer than an area comprising the fluid outlet. In some embodiments, the added layer depth is in the range of 0.05-0.1 mm, 0.1-0.3 mm, or 0.2-0.4 mm or any range larger, smaller or intermediate. Optionally, the cylindrical syringe comprises a right cylindrical shaped body. Alternatively, the syringe comprises a non-right cylindrical shape. Optionally, the plunger seal does not have a uniform face. For example, the plunger may not have a symmetrical surface surrounding its central axis, for example, one area of the plunger distal surface may be axially closer to the distal wall than the other area. Possibly, in an embodiment comprising a non-uniform plunger surface, the plunger does not rotate with respect to the syringe when being pushed onto the distal wall.

Additional measures to reduce fluid dead space include, in some embodiments, a thin fluid outlet path. Alternatively or additionally, fluid dead space is reduced by providing a collet having a relatively small volume, the collet mainly used for fluidly connecting between the needle path and the reservoir.

In some embodiments, when mass producing the syringe as provided herein, in a representative sample, at least 99% of the syringes and/or at least 97% and/or at least 90% of the syringes, the second contact area will be contacted before the first area comprising the fluid outlet. In some embodiments, a representative sample comprises at least 50 syringes, and/or at least 100 syringes, and/or at least 500 syringes, and/or at least 1000 syringes.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

1 High Level Mechanism for Reducing Fluid Dead Space

Figure 1:
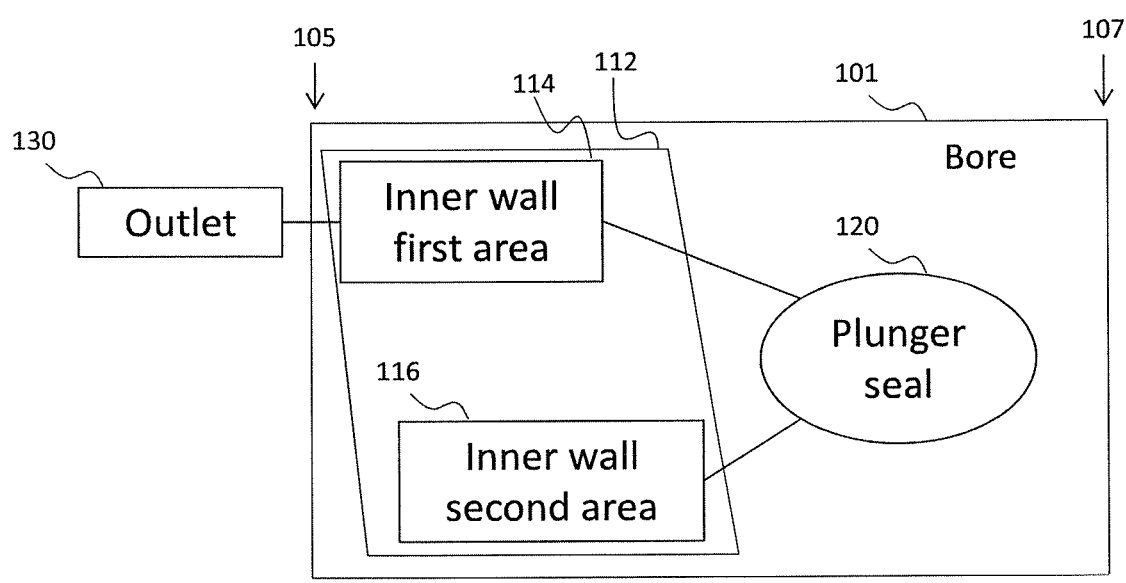
FIG. 1 is a block diagram illustrating a schematic mechanism of a syringe having a reduced fluid dead space, in accordance with some embodiments of the current invention.

Referring now to the drawings, FIG. 1 shows a block diagram illustrating a general schematic mechanism for reducing fluid dead space in a syringe having a cylindrical bore 101 fitting a plunger seal 120 and having an open proximal end 107 and an off-centered fluid outlet 130 at its distal end 105, in accordance with some embodiments of the invention.

In some embodiments, dead space is reduced by providing a distal inner wall 112 which is configured to meet a face of plunger 120 at a contact location which is offset to the fluid outlet location before contacting the location of the fluid outlet. By contacting an offset location first, fluid is potentially driven towards the uncontacted space between the inner wall and the plunger, the uncontacted space comprises the fluid outlet.

In some embodiments, a first area 114 of inner wall 112 comprises the fluid outlet and a second area 116 of inner wall 112 is configured to contact the surface of plunger 120 before the first area. For example, second area 116 is in some embodiments angled towards the surface of plunger 120. Alternatively or additionally, first area 114 is angled away from the surface of plunger 120. Alternatively or additionally, inner wall 112 is angled such that a mean direction defined by the inner wall cross-section is angled with respect to a mean direction of a cross-section of the plunger 120 face.

2 Exemplary Method for Reducing Dead Space

Figure 2:
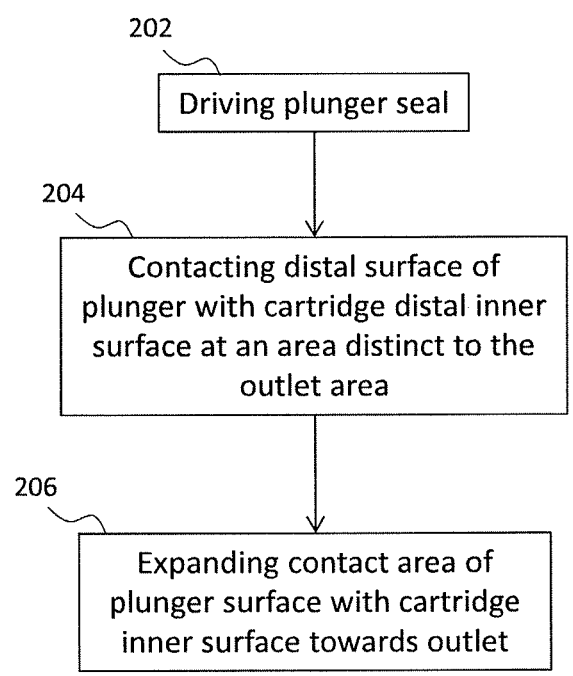
FIG. 2 is a flowchart illustrating a method for reducing fluid dead space in a syringe, in accordance with some embodiments of the current invention.

Reference is now made to FIG. 2, showing a flowchart exemplifying a method for reducing fluid dead space in a syringe having an off-centered fluid outlet, in accordance with some embodiments of the invention. In order to expel the fluid from the cartridge out through the fluid outlet, a plunger seal is driven 202 towards the distal portion of the cartridge, which contains the outlet.

One way to reduce fluid remaining inside the cartridge is to gather fluid from areas which are distinct from the area comprising the fluid outlet. Therefore, in some embodiments, the distal surface of the plunger seal is contacted with an area of the inner surface of the distal wall of the cartridge, which is distinct from an area comprising the off-centered outlet 204. Optionally, the inner surface is sized and shaped to be closer to the plunger seal distal surface at the area which is distinct from the outlet location.

In some embodiments, expanding the contact range of the plunger surface with the inner wall towards the outlet 206, is conducted by driving the plunger into the direction of the outlet. In some embodiments, in order to contact increasing portions of the inner wall, the plunger is elastically deformed against the inner surface of the distal wall.

In some embodiments, the distinct area from the outlet area is located at an opposite portion to the outlet, for example, if the outlet is located in proximity to an edge defined as the dorsal portion of the cartridge, the distinct area may range from the ventral portion of the cartridge. Alternatively or additionally, the distinct area can be closer to the cartridge edge than the outlet. For example, if the outlet is located in proximity to the dorsal portion of the cartridge, the area between the outlet and the dorsal edge may be considered distinct and, in some embodiments, this distinct area is shaped to be closer to the plunger than the outlet area. Optionally, the distinct area contacts at least 20%, and/or at least 30%, and/or at least 40%, and/or at least 50% of the distal surface of the plunger, before the plunger contacts the area comprising the biased fluid outlet.

3 Potential Fluid Path Resulting from a Reduced Dead Space Configuration

Figure 3:
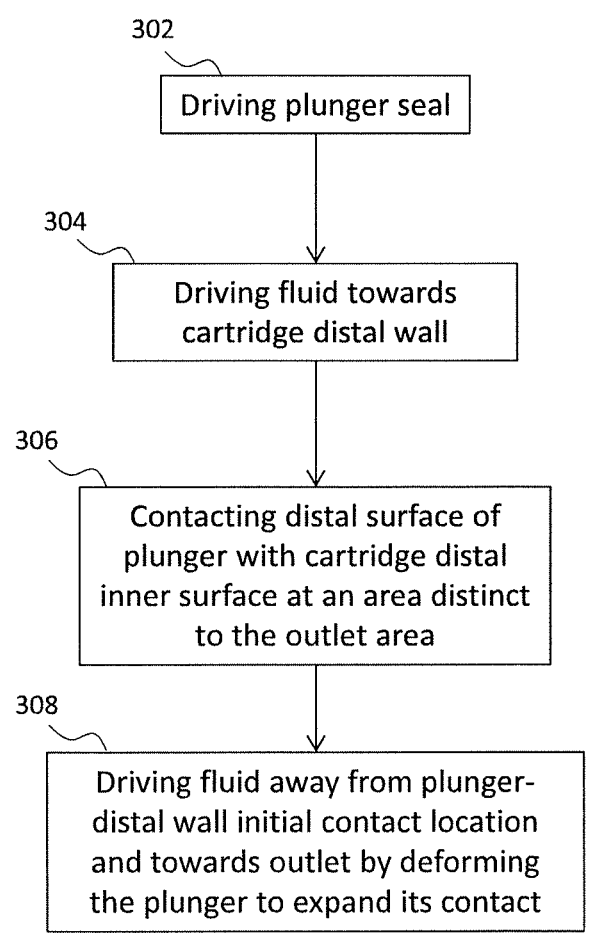
FIG. 3 is a flowchart illustrating the fluid dynamics resulting from the method shown in FIG. 2, in accordance with some embodiments of the current invention.

Reference is now made to FIG. 3, exemplifying a possible fluid dynamic path resulting from the configuration shown in FIG. 1 and/or the method exemplified in FIG. 2, in accordance with some embodiments of the invention.

Once the plunger is driven towards the distal portion of the cartridge 302, fluid contained in the cartridge is expelled towards the cartridge distal wall 304, optionally expelling through the off-centered outlet of the cartridge. In some embodiments, the fluid is expelled from the cartridge so long as the plunger is driven towards the distal edge including when the distal surface of the plunger initially contacts the inner surface of the cartridge distal wall at an area distinct to the area of the outlet 306.

In some embodiments, fluid continues to be expelled after the initial contact of the plunger surface with the inner surface of the distal wall, when fluid is driven away from the initial contact location and towards the outlet location 308, optionally by deforming the plunger to expand its contact range. In some embodiments, the plunger is deformed when force is exerted over it in the direction of the distal wall after the plunger's initial contact with a portion of the distal wall being closer to it. Due to the mechanical hindrance of the closer portion, the contacted portion of the plunger cannot advance anymore, but in some embodiments, the plunger distal surface elastically deforms when being forced onto the distal wall, resulting in an increased contact range.

In some embodiments, the mean direction of the distal inner wall results in fluid being expelled along that direction, which is tilted with respect to the mean direction of the distal surface of the plunger.

4 Exemplary Configuration and Dimensions of a Drug Delivery Device Having an Off-Centered Fluid Outlet Reference is now made to FIG. 4, schematically illustrating examples of asymmetric syringes useful, for example, in drug delivery devices, and utilized in some embodiments of the current invention.

Typical and/or exemplary dimensions of a drug delivery cartridge, such as syringe 409, are provided herein. In some embodiments the payload of reservoir and/or cavity 432 (for example in syringe 409) may include, for example between 0.5 and 2 ml and/or between 2 and 7 ml and/or between 7 and 6 ml and/or between 7 and 10 ml of a drug and/or of a placebo and/or of any bioactive and/or non-bioactive material. In some embodiments, the injector may discharge the entire payload as a single dose. A drug delivery device may include, for example, a patch injector, and/or an internally powered driver to drive the plunger and/or discharge the payload.

For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example, the driver may be designed to discharge the payload over a time period ranging between 20 and 120 seconds and/or between 120 and 600 seconds and/or between 600 seconds and an hour and/or between an hour and a day and/or longer.

In general, discharge may be driven by a driver. An internally powered driver may be powered by various mechanisms including for example a motor as discussed, including for example a DC motor, an actuator, a brushless motor, and/or a transmission including for example a telescoping assembly and/or a threaded element and/or a gear and/or a coupling and/or an elastic mechanism (for example a spring and/or a rubber band) and/or an expanding gas and/or a hydraulic actuator.

A drug delivery device in accordance with some embodiments of the present invention may include a reservoir part as discussed. For example, a reservoir may include a medicine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle, typically hollow, may optionally be connected to the syringe bore. For example, the hollow of the needle may be in fluid communication with the interior of the bore. The needle may optionally be rigidly attached to an extension at the distal end of the bore.

In some embodiments, a plunger may slide axially along the inside of the bore to discharge a medicine payload. For example, the medicine may be discharged through the hollow needle. The protruding tip of the needle may be oriented at an angle to the axis of the bore.

Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

For example, drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example the mechanism may include a snap that gives way at 70 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. During injection, the linear movement of a plunger may range for example between 10-50 mm. The length of movement of the plunger may vary for example with the volume of medicine to be injected that may range for example between 0.5 to 3 ml.

In some embodiments the reservoir may have a length ranging for example between 20 and 72 and/or 72 and 78 mm and/or 78 and 80 mm and/or 80 and 200 mm. In some embodiments an internal cylindrical space of a reservoir may have an average width ranging for example between 1 and 3 mm and/or 3 and 10 and/or 10 and 15 mm and/or 15 and 25 mm and/or 25 and 50 mm. Optionally a reservoir may have a circular cross section such that width is the diameter of the circle. In some embodiments an extension may have a straight end portion with a length ranging for example between 1 and 3 mm or 3 and 7 mm or 7 and 8 or 8 and 10 mm or 10 and 15 mm or 15 and 50 mm. In some embodiments the exposed straight portion of a needle may have a length ranging for example between 1 and 5 mm or 5 and 7 mm or 7 and 10 mm or 10 and 20 mm.

In some embodiments a fluid path between an extension and a reservoir cavity may include a 27 gauge needle or a needle ranging between 25 and 30 gauge or a needle ranging between 20 and 25 gauge or a needle ranging between 30 and 32 gauge. In some embodiments a needle protruding from the extension may include a 27 gauge needle or a needle ranging between 25 and 30 gauge or a needle ranging between 20 and 25 gauge or a needle ranging between 30 and 32 gauge.

Figure 4B:
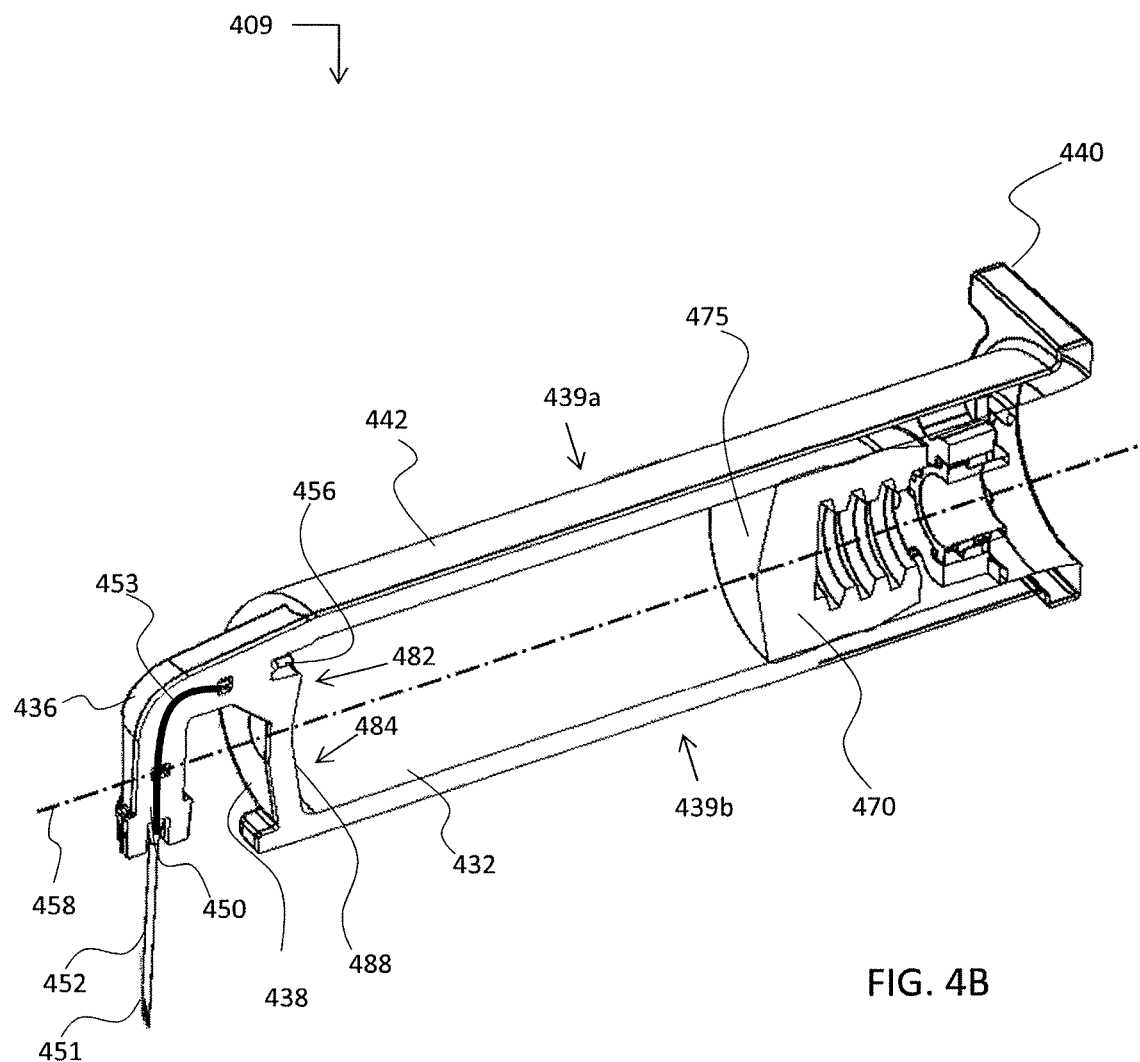

Reference is now made to FIG. 4B, schematically illustrating a cross section of a bore designed for reducing dead space, in accordance with some embodiments of the current invention. In some embodiments a fluid path 450 connecting between cavity 432 of bore 442 and hub 436 may pass through and/or be molded into syringe 409. Optionally (for example as illustrated in FIG. 4B), a metal needle 452 forms a portion of fluid path 450. Optionally dead space in fluid path 450 is reduced by having the entire path inside needle 452 (reducing dead space in the plastic mold). For example an embedded portion 453 of needle 452 forms a bent fluid path 450 to a protruding portion 451. Protruding portion 451 optionally protrudes straight out of hub 436 at substantially a right angle to axis 458 of the cavity and/or axis 432 of bore 442. The protruding end of needle 452 is optionally beveled and/or sharpened to facilitate insertion through the skin of a subject.

In some embodiments, the size of the end mount holding the end of needle 452 in cavity 432 is made small to reduce the dead space left over after molding. Optionally, an end mount may include a pin and/or a collet. For example, a collet may have a concave and/or conical inner face that grasps the end of needle 452. Alternatively or additionally, a pin may have a convex and/or conical face that fits into the hollow of needle 452 and/or is self-aligning as it is inserted. For example a pin may include an inner convex portion that fits into the needle 452 and/or an outer concave portion that positions needle 452. Before molding, the outer concave portion of the pin may position needle 452 in order to insert the inner convex portion of the pin into the hollow of needle 452. Then the outer concave portion may be retracted before molding. Optionally during molding only the inner portion of the pin remains in the mold. After molding the inner pin is optionally removed leaving a reduced dead space when a drug is discharged from the syringe.

5 Exemplary Inner Distal Wall Configurations

FIGS. 5A-5E exemplify possible configurations for a distal inner wall, resulting in a plunger-wall interface potentially reducing fluid dead space, in accordance with some embodiments of the invention.

For illustrative purposes and for portraying useful axis definitions, FIGS. 5A and 5B schematically illustrate a medicinal syringe having a bore with an inner distal wall shaped to fit a plunger distal face, both having substantially non-angled and aligned mean directions, wherein FIG. 5B is an enlarged view of the marked circle region in FIG. 5A.

FIG. 5A schematically illustrates a side view of a cross-section of an example of the above described syringe. In some embodiments, the syringe comprises cylindrical bore 442 fitting a plunger seal 470. Optionally, the bore has a proximal end 440 which is open. In some embodiments, at its distal end 438, bore 442 includes a wall having inner surface 488, optionally inner surface 488 has a different profile and/or cross-section than the outer surface of distal end 438. In some embodiments, bore 442 comprises an off-centered fluid outlet 456, optionally fluidly connecting reservoir 432 with path 450, which is optionally bent with respect to the central axis 458 of bore 442. In some embodiments, path 450 is bent such that a needle tip 451 is directed towards the ventral side 439b of bore 442. Optionally, in order to allow as much space for bent path 450, the off-centered fluid outlet is biased to the dorsal side of bore 442.

In some embodiments, plunger 470 comprises a distal face 475 having an interface sized and shaped to contact at least a portion of inner surface 488. Optionally the inner surface 488 is shaped such that an initial plunger-inner surface contact location is offset to a location of a fluid outlet. In some embodiments, distal surface 475 is convex. In some embodiments, inner surface 488 is concave. In some embodiments, the opening angle defined by inner surface 488 is substantially the same as the opening angle defined by distal surface 475.

Depicted below, with reference to FIGS. 5B-5E, are various areas of inner surface 488 with regards to its matching to distal surface 475, having various tilting angles and/or indentations and/or mean directions.

FIG. 5B illustrates a non-angled example, showing an enlarged view of the marked circular area in FIG. 5A. Exemplified are the mean directions 584 and 582 of the two distinct areas 484 and 482 of inner surface 488. In the non-angled example of FIG. 5B, inner surface 488 has a mean direction which fits with the mean direction of plunger distal surface 475. More specifically, when plunger distal surface 475 is symmetrical around central axis 458, in this example both the dorsal area 482 and the ventral area 484 have the same mean directions 584 and 582, which also fit with the mean directions of the dorsal portion and the ventral portion of the distal surface 475.

FIG. 5C illustrates a tilting of both the dorsal area 482 and the ventral area 484. Shown is tilting of dorsal area 482 with respect to the original mean direction 582 by angle A. Also shown is tilting of dorsal area 484 with respect to the original mean direction 584 by angle B. In some embodiments, the area comprising the outlet, for example in this embodiment area 482, is tilted away from the plunger, while the area distinct from the area comprising the outlet, for example in this embodiment area 484, is tilted towards the plunger. Optionally, angles A and B are the same. Alternatively, angles A and B tilt to a different extent. In some embodiments, area 482 and/or area 484 have a dorsal-ventral cross section which is curved. Preferably but not compulsory, the curve of area 482 and/or 484 is concave, curving away from the plunger, potentially preventing more dead space.

FIG. 5D illustrates tilting of only the ventral area 484 in angle B. In the illustrated embodiment, area 484 is distinct from the area comprising the outlet 456. It is usually desired that fluid will be expelled from areas surrounding outlet 484, and therefore, in some embodiments, area 484 is tilted towards plunger surface 475, potentially to contact its surface first and drive the fluid away towards the outlet area 482.

FIG. 5E illustrates tilting of only the dorsal area 482 in angle A. In the illustrated embodiment, area 482 comprises the outlet 456. Since it is usually desired that fluid will be expelled from areas surrounding outlet 484, in this embodiment area 482 is tilted away from plunger surface 475, leading to area 484 being closer to plunger surface 475 and potentially contact it first.

6 Plunger Interface with Reduced Dead Space

FIG. 6 is a cross-sectional view of a distal section 609 of a syringe with an angled inner distal wall 678 and angled hub 436 mounted off center on a cylindrical cavity 432 in accordance with some embodiments of the current invention. For example the fluid path may connect to cavity 432 of bore 442 at a location of off centered outlet 456. In some embodiments, a distal surface of a plunger seal 670 may have a convex substantially conical shape with an opening angle 668. In some embodiments, an inner surface 678 of distal wall of cylindrical cavity 432 may have a substantially concave conical shape with an opening angle 666. Optionally opening angle 668 of the distal face of plunger seal may be sharper than opening angle 666 of the inner distal wall 678 of cylindrical cavity 432. Optionally inner distal wall 678 of a cylindrical cavity 432 may be angled with respect to the distal face of plunger seal 670, for example, inner distal wall 678 may have a mean direction which is offset to a mean direction defined by the plunger surface 670. In order to better show molded features, an optional needle 452 forming a boundary of fluid path 450 is not shown in FIG. 6.

In some embodiments, features may be configured to avoid fluid getting trapped in dead space between the distal face plunger seal 670 and the inner distal wall 678 of cylindrical cavity 432. For example, the shape of the distal face of plunger seal 670 and/or the distal inner wall 678 of cavity 432 may be configured to push fluid towards the opening of fluid path 450 as plunger seal 670 approaches the inner distal wall of cavity 432. For example in some embodiments, where the fluid path 450 connects to cavity 432 near an outer edge of cavity 432, opening angle 668 of the distal face of plunger seal may be sharper than opening angle 666 of the inner distal wall 678 of cylindrical cavity 432. For example the opening angle of the distal face of plunger seal 670 may range between 0 to 1 degree less and/or between 1 to 3 degree less and/or between 1 to 5 degree less and/or between 5 to 10 degree less and/or between 10 to 30 degree less than the opening angle of distal wall 678 of cavity 432. Alternatively or additionally, in some embodiments, where the fluid path 450 connects to cavity 432 near the axis 458 of cavity 432 (for example as illustrated in FIG. 5), opening angle 668 of the distal face of plunger seal may be less sharp than opening angle 666 of the inner distal wall 678 of cylindrical cavity 432.

In some embodiments, where the fluid path 450 connects to cavity 432 near an outer edge of cavity 432, the inner distal wall 678 of a cylindrical cavity 432 connecting to fluid path 450 may be angled away from the distal face plunger seal 670. For example, plunger seal 670 and/or the distal face thereof may be aligned with axis 458 of cylindrical cavity 432 while an axis 680 of the conical distal inner wall 678 is at an angle of between 0 to 0.1 degree and/or between 0.1 to 1 degree and/or between 1 to 3 degrees and/or between 3 to 10 degrees and/or between 10 to 30 degrees of axis 458 and/or an axis of plunger seal 670 and/or an axis of a conical face of plunger seal 670. Alternatively or additionally distal inner wall 678 may not be right conical and/or may not be conical and/or may not be symmetrical. For example, fluid path 450 may connect to inner distal wall 678 between the center 638 and the outer edge and/or the portion of inner distal wall 678 connecting to path 450 may be indented slightly distally with respect to the rest of inner distal wall 678, resulting in axis 582 which is tilted with respect to axis 671 defined by the outer portion of distal surface 670 by angle a. In some embodiments, a has a range between 0 to 0.1 degree and/or between 0.1 to 1 degree and/or between 1 to 3 degrees and/or between 3 to 10 degrees and/or between 10 to 30 degrees. For example, in some embodiments, fluid path 450 may connect near the dorsal side 439 a of cavity 432. Then the axis of inner distal wall 678 is optionally tipped at a positive angle with respect to axis 458 and/or an axis of a conical face of plunger seal 670.

In some embodiments, when inserted into cavity 432, plunger seal 670 may be substantially symmetric around axis 458. For example, plunger seal 670 may have a sealing surface 672 and/or a stabilizing surface 674 in contact with the inner side walls of cavity 432. Optionally, plunger seal 670 may include a plunger driver mount 676. Plunger driver mount 676 is optionally coaxial to cavity 432.

In some embodiments, for an off center fluid path, the distal face of a plunger seal 670 may have a concave substantially conical shape, and an inner distal wall 678 of a cylindrical cavity 432 may have a substantially convex conical shape. Optionally, the opening angle of the distal face of plunger seal may be less sharp than opening angle of the inner distal wall 678 of cylindrical cavity 432.

7 Variably Angled Wall

Reference is now made to FIG. 7, illustrating walls having variable angles with respect to the central longitudinal axis of the syringe bore, in accordance with some embodiments of the invention.

FIG. 7A illustrates an inner surface 488 having dorsal side 439a and ventral side 439b, and having a wall which defines variable angles around axis 458, in accordance with some embodiments of the invention. In some embodiments, the first area 482 of said inner surface, defined as the area comprising outlet 456, is shaped as a portion of a first cone, having apex angle 2β, and a second area 482 of said inner surface, defined as an area distinct from the outlet area, is shaped as a portion of a second cone, having apex angle 2α. In some embodiments, central axis 458 splits each of the apexes such that the angle between the mean direction of area 482 and axis 458 is in angle β and the angle between the mean direction of area 484 and axis 458 is in angle α. In some embodiments, the second cone has a sharper apex angle than the first cone, i.e. α<β.

FIGS. 7B and 7C show polar charts which illustrate the transitions 702a and 702b found between the first area 482 of said inner surface and the second area 484 of said inner surface, wherein point C corresponds to the dorsal side 439a and point G corresponds to the ventral side 439b. In some embodiments, the transition between area 482 and area 484 is continuous, as exemplified in FIG. 7B. Alternatively or additionally, the transition between area 482 and area 484 is non-continuous, and optionally has the shape of substantially a step graph. In some embodiments, the transition between area 482 and area 484 in one side, such as A, is the same as the transition in the other side, such as B, maintaining symmetry at least across the dorsal-ventral line. Alternatively, the transition is different in each side.

8 Flat Faced Plunger Seal

FIG. 8 schematically illustrates a medicinal syringe 800 having a plunger seal 870 with a flat distal surface 875, in accordance with some embodiments of the invention. In some embodiments, syringe 800 comprises cartridge 842 for containing fluids, which has a distal end 838, ending in inner distal surface 888 comprising a dorsal side 882 and a ventral side 884. In some embodiments, proximal to the dorsal side 882 is located the fluid outlet 856, which is located off-centered relative to central axis 858. Optionally, the fluid is expelled through outlet 856 and out through fluid path 850.

In some embodiments, in order to drive fluid towards outlet 856, while having reduced fluid remaining in the cartridge 842, and specifically in the space between inner surface 888 and plunger surface 875, the ventral portion 884 of surface 888 is tilted towards surface 875. Alternatively or additionally, the dorsal portion 842 is tilted away from surface 875. The tilting results in the mean direction 882 of the inner surface 888 to be offset to the mean direction 887 of the plunger surface 875.

9 General

It is expected that during the life of a patent maturing from this application many relevant syringe devices will be developed and the scope of the term syringe and/or cartridge is intended to include all such new technologies a priori.

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical syringe comprising:
   a cylindrical bore having a proximal opening, a distal wall having an inner surface, an interior surface extending from said proximal opening to said distal wall, and a central axis, said inner surface having a first area and a second area distinct from said first area, said distal wall of said cylindrical bore defining an outlet, said outlet being spaced from said central axis toward said first area and away from said second area;
   a hub extending from said distal wall, said hub defining a hub outlet and a fluid path extending from said outlet of said cylindrical bore to said hub outlet; and
   a plunger seal positioned within and coaxial to said cylindrical bore, said plunger seal having a side surface configured to slidingly engage the interior surface of the cylindrical bore, a distal surface defining a center, the distal surface extending either perpendicular to said central axis or proximally as it extends radially from said center to said side surface;
   wherein when said plunger seal is fitted within said cylindrical bore with said distal surface facing said inner surface of said distal wall of said cylindrical bore, said second area of said inner surface is axially closer to said distal surface of said plunger seal than said first area, in a direction parallel to said central axis of said cylindrical bore, allowing said second area to contact said distal surface of said plunger seal before said distal surface contacts said first area.

2. The pharmaceutical syringe of claim 1, wherein a mean direction of said inner surface is tilted with respect to said central axis.

3. The pharmaceutical syringe of claim 2, wherein said mean direction of said inner surface is tilted at an angle ranging from about 1 to about 5 degrees with respect to said central axis.

4. The pharmaceutical syringe of claim 1, wherein said distal surface of said plunger seal comprises a convex shape with respect to the plunger seal.

5. The pharmaceutical syringe of claim 4, wherein said inner surface comprises a concave shape with respect to the plunger seal.

6. The pharmaceutical syringe of claim 5, wherein said inner surface comprises a conical shape, and wherein an opening angle of said inner surface is less sharp than an opening angle of said convex shape of said distal face of said plunger seal.

7. The pharmaceutical syringe of claim 1, wherein said inner surface is not radially symmetrical.

8. The pharmaceutical syringe of claim 1, wherein a mean direction of said first area of said inner surface is not parallel to a mean direction of said distal surface of said plunger seal, when said plunger seal being coaxial to said bore.

9. The pharmaceutical syringe of claim 1, wherein a mean direction of said second area of said inner wall is parallel to a mean direction of said distal surface of said plunger seal, when said plunger seal being coaxial to said bore.

10. The pharmaceutical syringe of claim 1, wherein a distance between a mean outer edge of the distal surface of the plunger seal and a mean outer edge of said second area being smaller than a distance between said mean outer edge of the distal surface of the plunger seal and a mean outer edge of said first area.

11. The pharmaceutical syringe of claim 1, wherein a transition between a surface of said first area of said inner surface and a surface of said second area of said inner surface is continuous.

12. The pharmaceutical syringe of claim 1, wherein said first area of said inner wall comprising said fluid outlet is located in proximity to an edge of said bore and said second area is located in proximity to the opposite edge of said bore.

13. The pharmaceutical syringe of claim 1, further comprising a bent fluid path originating from said fluid outlet.

14. A method for reducing fluid dead space in a pharmaceutical syringe comprising a cylindrical bore with a proximal opening and a distal end including a fluid outlet spaced from a central axis of the cylindrical bore and an interior surface extending from said proximal opening to said distal end, and a hub extending from said distal end of said cylindrical bore, said hub defining a hub outlet and a fluid path extending from said outlet of said cylindrical bore to said hub outlet, and said cylindrical bore fitting a plunger seal having a distal surface, the plunger seal having a side surface configured to slidingly engage the interior surface of the cylindrical bore, the method comprising:
   driving said plunger seal towards said distal end of said cylindrical bore, the distal surface of said plunger seal extending either perpendicular to said central axis or proximally as it extends radially from said central axis to said side surface;
   contacting a portion of said distal surface of said plunger seal with a portion of an inner surface of a wall of said distal end of said cylindrical bore at a contact area distinct from an area comprising the fluid outlet; and expanding a range of contact from said contact area towards the location of the fluid outlet while expelling fluid in a mean direction which is tilted with respect to a mean direction of said distal surface of said plunger seal, wherein said contacting at said contact area comprises contacting said distal surface of said plunger seal before contacting said area comprising the fluid outlet.

15. The method of claim 14, wherein said contacting comprises initially contacting at said contact area being a peripheral edge of said inner surface, said peripheral edge being distinct to said area comprising said fluid outlet.

16. The method of claim 14, wherein said expanding comprises expanding said range of contact from said peripheral edge, through a center portion of said inner wall and onto said area comprising said fluid outlet.

17. The method of claim 14, wherein said expanding said range of contact is conducted by elastically deforming said plunger seal.

18. The method of claim 14, wherein said expanding said range of contact results in driving fluid away from said contact location towards said location of said fluid outlet.

19. The method of claim 14, further comprising ending said driving of said plunger seal at a force ranging between about 5 N and about 25 N.

20. The method of claim 19, wherein following said ending, a volume of a fluid dead space between said plunger seal and said inner wall ranges between about 0.01 ml and about 0.5 ml.

* * * * *